US00PP37501P2

(12) United States Plant Patent
Mathey

(10) Patent No.: US PP37,501 P2
(45) Date of Patent: Jun. 30, 2026

(54) ***BUDDLEIA* PLANT NAMED 'SMNBDMO'**

(50) Latin Name: *Buddleia davidii*
Varietal Denomination: SMNBDMO

(71) Applicant: Spring Meadow Nursery Inc, Grand Haven, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,896

(22) Filed: Oct. 28, 2025

(51) Int. Cl.
*A01H 6/00* (2018.01)
*A01H 5/00* (2018.01)

(52) U.S. Cl.
USPC ..... Plt./242

(58) Field of Classification Search
USPC ..... Plt./226, 242
See application file for complete search history.

(56) References Cited

U.S. PATENT DOCUMENTS

PP28,836 P2 * 1/2018 Wood ..... A01H 6/00
Plt./242

* cited by examiner

*Primary Examiner* — Karen M Redden

(57) ABSTRACT

A new and distinct cultivar of *Buddleia* plant named 'SMNBDMO' is disclosed, characterized by large conical inflorescences of fragrant, dark royal purple flowers with burnt orange throats. Plants have well-branched, tidy habits, and excellent flower coverage. The new cultivar is a *Buddleia*, typically produced as an outdoor ornamental plant.

2 Drawing Sheets

Latin name of the genus and species: *Buddleia davidii*.
Cultivar denomination: 'SMNBDMO'.

BACKGROUND OF THE INVENTION

The new cultivar is a product of a planned breeding program conducted by the inventor to produce *Buddleia davidii* with abundant flower panicles, and compact, well-branched habits. The open pollination resulting in the new cultivar was made in summer of 2020 at a nursery in Grand Haven, Michigan.

The seed parent is the unpatented cultivar *Buddleia davidii* 'Black Knight'. The pollen parent is unknown. The new cultivar was found and selected by the inventor in summer of 2022 at the same nursery in Grand Haven, Michigan. Asexual reproduction of the new cultivar 'SMNBDMO' was first performed during summer of 2022 in Grand Haven, Michigan, by softwood cuttings. Through subsequent propagation, multiple additional generations have been reproduced, having shown that the unique features of this cultivar are stable and reproduced true to type.

SUMMARY OF THE INVENTION

The cultivar 'SMNBDMO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNBDMO'. These characteristics in combination distinguish 'SMNBDMO' as a new and distinct *Buddleia* cultivar:

1. Dark royal purple flowers with burnt orange throats.
2. Large, slender, well-formed conical flower panicles.

3. Floriferous; excellent flower coverage.
4. Highly fragrant flowers.
5. Well-branched, tidy habit.
6. Excellent container performance.

PARENT COMPARISON

Plants of 'SMNBDMO' are similar to plants of the seed parent in most horticultural characteristics, however, plants of 'SMNBDMO' differ in the following:

1. Flower color of the new cultivar is a darker than the flower color of the seed parent.
2. Plants of the new cultivar are smaller at maturity than plants of the seed parent.
3. Plants of the new cultivar are more compact and tidy than plants of the seed parent.

COMMERCIAL COMPARISON

Plants of 'SMNBDMO' can be compared to plants of the commercial cultivar *Buddleia davidii* 'Dark Dynasty', U.S. Plant Pat. No. 27,834. Plants of 'SMNBDMO' are similar to plants of 'Dark Dynasty' in most horticultural characteristics, however, plants of 'SMNBDMO' differ in the following:

1. Panicles of the new cultivar are larger than the panicles of this comparator.
2. Panicle apex of the new cultivar is tapered/pointed, while the panicle apex of this comparator is more rounded.

BRIEF DESCRIPTION OF THE PHOTOGRAPHS

Figure 1:
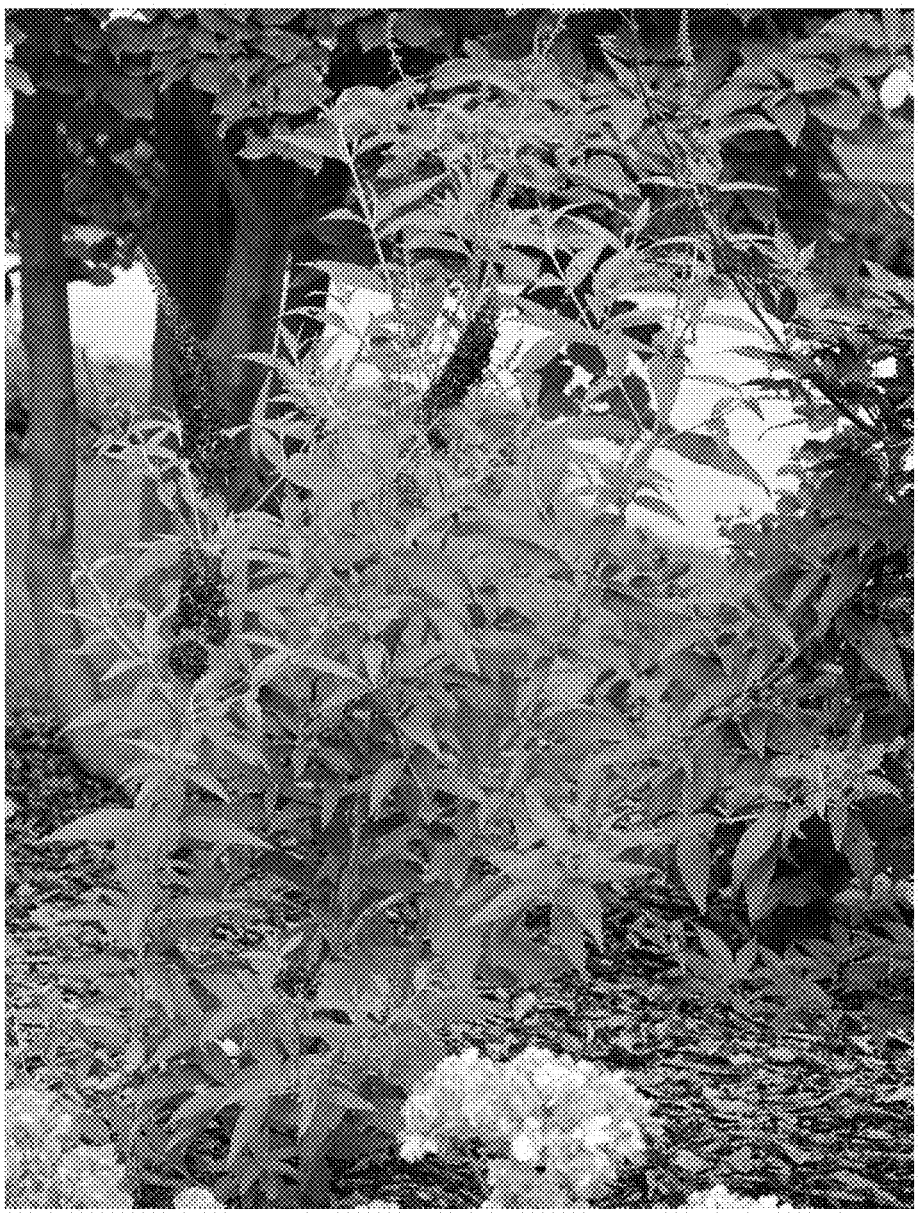

The accompanying photograph in FIG. 1 illustrates in full color a typical plant of 'SMNBDMO' grown outdoors in Grand Haven, Michigan. This plant is approximately 2 years old and is planted in the ground.

Figure 2:
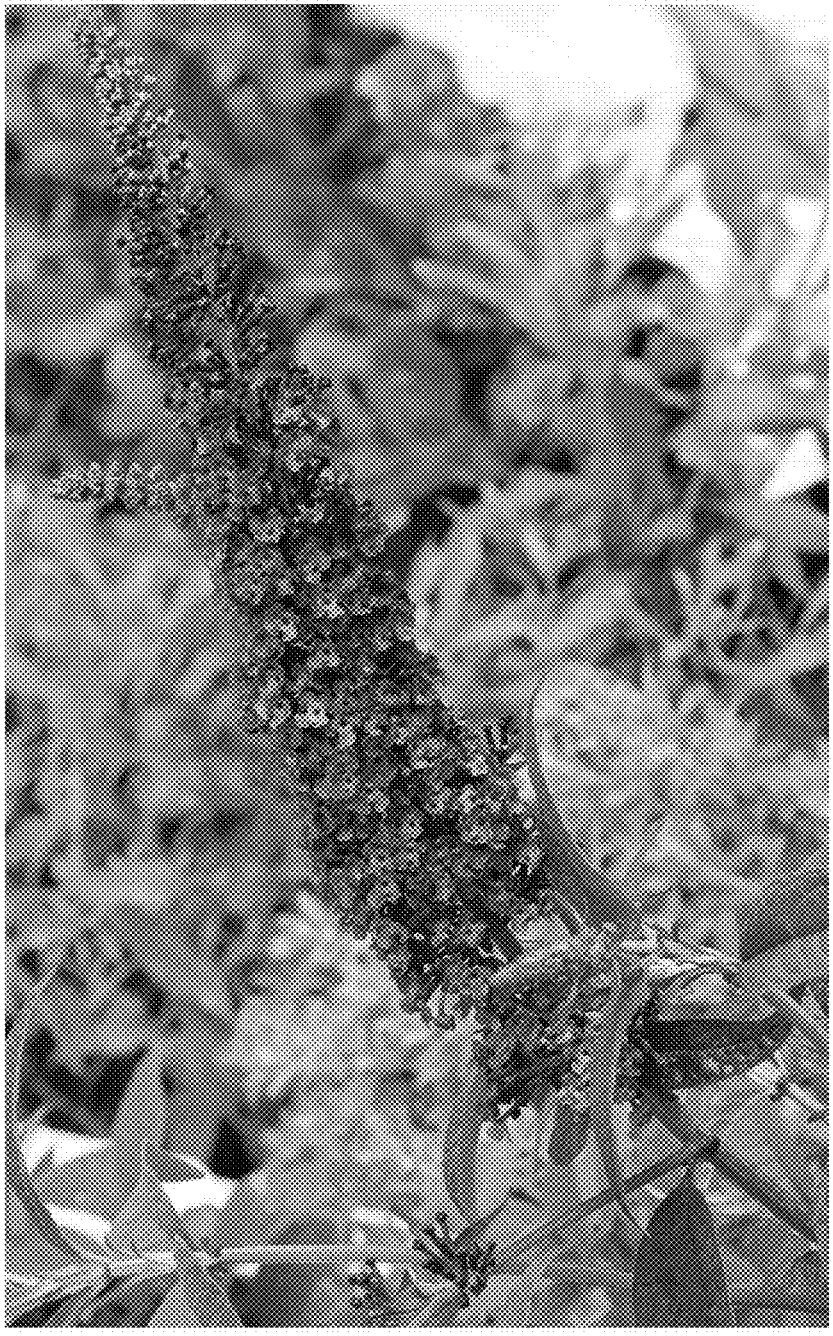

FIG. 2 illustrates in full color a close up of an inflorescence of 'SMNBDMO'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'SMNBDMO' plants grown in a poly-greenhouse in Grand Haven, Michigan. The plants were 2 years old. Temperatures ranged from 5° C. to 10° C. at night to 18° C. to 27° C. during the day. No artificial light, photoperiodic treatments were given to the plants. Measurements and numerical values represent averages of typical plant types. Botanical classification: *Buddleia davidii* 'SMNBDMO'.

PROPAGATION

Typical method: Softwood cuttings.
Root initiation: 14 days in summer at 25° C.
Time to produce rooted cutting: About 40 days in summer at 25° C.
Roots: Dense, freely branching, fine, fibrous. Tan in color, not accurately measured with R.H.S. chart.

PLANT

Plant type: Perennial flowering shrub.
Growth habit: Upright and compact.
Shape: Elliptic.
Height: 75 cm.
Plant spread: 65 cm.
Pot size of plant described: 2 gallon.
Age of plant described: 2 to 3 years.
Stem:
- *Branching*.—Basal and lateral.
- *Pinching*.—Some required to encourage well-rounded habit.
- *Number of lateral branches*.—10 to 20.
- *Shape*.—Square.
- *Color*.—Immature: RHS Yellow-Green 148C. Mature: RHS Grey-Brown 199C.
- *Length*.—45 cm.
- *Width*.—4 mm.
- *Aspect*.—0° to 30° from vertical.
- *Strength*.—High.
- *Texture*.—Pubescent, colored RHS Grey-Brown 199C.
- *Internode Length*.—6 cm.

FOLIAGE

Leaf:
- *Arrangement*.—Opposite, single.
- *Shape*.—Narrowly elliptic to oblong.
- *Length*.—12 cm.
- *Width*.—3.5 cm.
- *Apex*.—Acuminate.
- *Base*.—Cuneate.
- *Margin*.—Serrulate.
- *Texture of top surface*.—Very lightly pubescent; coriaceous.
- *Texture of bottom surface*.—Lightly pubescent, coriaceous with raised venation.
- *Pubescence*.—Yes, both sides.
- *Color*.—Young Foliage, Upper Side: RHS Green NN137A. Young Foliage, Under Side: RHS Greyed-Green 195B. Mature Foliage, Upper Side: RHS Green NN137A. Mature Foliage, Under Side: RHS Greyed-Green 195B.

Venation:
- *Type*.—Pinnate.
- *Color*.—Mature, Upper Side: RHS Yellow-Green 148C. Mature, Under Side: RHS Yellow-Green 148C.

Petiole:
- *Length*.—4 mm.
- *Width*.—2 mm.
- *Color*.—Upper Side: RHS Yellow-Green 148C. Under Side: RHS Yellow-Green 148C.
- *Texture*.—Upper Side: Pubescent. Under Side: Pubescent.

FLOWER

Natural flowering season: Summer.
Flower arrangement: Terminal inflorescences.
Inflorescence type: Panicle.
Height: 30 cm.
Diameter: 5 cm.
Quantity of flowers per inflorescence: About 1500.
Quantity of flowers per plant: Around 4 mature inflorescences per plant, though each lateral branch is terminated with 3-5 inflorescences in various stages of development which will open as the bloom period progresses.
Quantity of buds per plant: Around 500 per inflorescence.
Quantity of flowers and buds per plant: Tens of thousands.
Fragrance: Very sweet and honey-like. Moderate intensity.
Flower:
- *Type or form*.—Salverform.
- *Aspect*.—Outward.
- *Length*.—1 cm.
- *Diameter*.—8 mm.
- *Depth*.—8 mm.
- *Persistence*.—Persistent.
- *Longevity*.—About 1 week.

Bud:
- *Length*.—7 mm.
- *Diameter*.—1 mm.
- *Shape*.—Oblong with a flared, square tip.
- *Color*.—RHS Purple 79A, Violet-Blue N92A at tip.

Petals:
- *Number*.—4.
- *Appearance*.—Soft, vibrantly colored; arranged in a whorl around brightly colored throat.
- *Arrangement*.—Cruciform.
- *Shape*.—Globose.
- *Tip*.—Obtuse.
- *Base*.—Fused.
- *Margin*.—Entire.
- *Length*.—3 mm.
- *Width*.—3 mm.
- *Texture*.—Upper side: Soft and silky. Under side: Soft and silky.

*Color*.—When Opening, Upper Side: RHS Purple 79B with Violet-Blue N92D at the margin. When Opening, Under Side: RHS Purple 79B with Violet-Blue N92D at the margin. Fully Opened, Upper Side: RHS Purple 79B with Violet-Blue N92D at the margin. Fully Opened, Under Side: RHS Purple 79B with Violet-Blue N92D at the margin. Throat Color: RHS Yellow-Orange 15A. Tube Color: RHS Purple 79A.

Sepals:
*Number*.—4.
*Arrangement*.—Whorl; narrowly triangular; fairly inconspicuous.
*Shape*.—Deltate.
*Tip*.—Acute.
*Base*.—Fused.
*Margin*.—Entire.
*Length*.—1 mm.
*Width*.—0.5 mm.
*Texture*.—Upper side: Glabrous. Under side: Glabrous.
*Color*.—Mature, Upper Side: RHS Green 138A. Mature, Under Side: RHS Green 138A.

Calyx:
*Shape*.—Oblong, with narrow, triangular sepals.
*Length*.—3 mm.
*Diameter*.—1 mm.

Peduncle:
*Terminal length*.—30 cm.
*Terminal diameter*.—5 mm.
*Angle*.—0° from vertical.
*Strength*.—High.
*Texture*.—Moderately pubescent.
*Color*.—RHS Yellow-Green 144A.

Pedicel:
*Length*.—1 cm.
*Diameter*.—1 mm.
*Angle*.—45° from vertical.
*Strength*.—Moderate.
*Texture*.—Moderately pubescent.
*Color*.—RHS Yellow-Green 144A.

REPRODUCTIVE ORGANS

Stamens:
*Number*.—2.
*Filament length*.—No filament, anthers fused directly to interior of throat.

Anthers:
*Shape*.—Linear.
*Length*.—1 mm.
*Color*.—RHS Yellow 4D.
*Pollen amount*.—Moderate.
*Pollen color*.—RHS Yellow 4D.

Pistil:
*Number*.—1.
*Length*.—2 mm.

Stigma:
*Shape*.—Linear.
*Color*.—RHS Yellow-Green 144B.
*Style length*.—1.5 mm.
*Style color*.—RHS Yellow-Green 144B.
*Ovary color*.—RHS Yellow-Green 144B.

OTHER CHARACTERISTICS

Fruit and seed: Not observed to date.

Disease resistance: Resistance and susceptibility to typical diseases and pests of *Buddleia* not observed.

Drought tolerance and cold tolerance: Hardy to USDA Zones 5 to 9.

What is claimed is:

1. A new and distinct cultivar of *Buddleia* plant named 'SMNBDMO' as herein illustrated and described.

* * * * *